US00PP14993P2

(12) United States Plant Patent
Lommerse

(10) Patent No.: US PP14,993 P2
(45) Date of Patent: Jul. 6, 2004

(54) DAHLIA PLANT NAMED 'BRONZE AMAZON'

(50) Latin Name: *Dahlia variabilis*
Varietal Denomination: Bronze Amazon

(75) Inventor: Henry Lommerse, Mariahout-Laarbeek (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 10/666,275

(22) Filed: Sep. 17, 2003

(51) Int. Cl.[7] ..... A01H 5/00
(52) U.S. Cl. ..... Plt./321

(58) Field of Search ..... Plt./321

(56) References Cited

PUBLICATIONS

UPOV–ROM GTITM Computer Database 2003/05, GTI Jouve Retrieval Software, Citation for 'Bronze Amazon'.*

* cited by examiner

*Primary Examiner*—Bruce R. Campell
*Assistant Examiner*—Annette H Para
(74) *Attorney, Agent, or Firm*—C. A. Whealy

(57) ABSTRACT

A distinct cultivar of Dahlia plant named 'Bronze Amazon', characterized by its upright, compact and rounded plant habit; freely basal branching habit; semi-double type inflorescences; and golden yellow and bright orange bi-colored ray florets with bright yellow-colored disc florets.

1 Drawing Sheet

Botanical classification/cultivar designation: *Dahlia variabilis* cultivar Bronze Amazon.

BACKGROUND OF THE INVENTION

The present Invention relates to a new and distinct cultivar of Dahlia plant, botanically known as *Dahlia variabilis*, commercially referred to as a pot-type Dahlia, and hereinafter referred to by the cultivar name Bronze Amazon.

The new Dahlia is a product of a planned breeding program conducted by the Inventor in Venhuizen, The Netherlands. The objective of the breeding program is to create new pot-type Dahlia cultivars with desirable inflorescence form and attractive ray and disc floret coloration.

The new Dahlia originated from a cross-pollination made by the Inventor on Jul. 15, 1998 of a proprietary *Dahlia variabilis* selection identified as code number 96.2580, not patented, as the female, or seed, parent with a proprietary *Dahlia variabilis* selection identified as code number 98.3930, not patented, as the male, or pollen, parent. The new Dahlia was discovered and selected by the Inventor as a single flowering plant within the progeny of the stated cross-pollination in a controlled environment in Venhuizen, The Netherlands, during the spring of 1999.

Asexual reproduction of the new Dahlia by vegetative tip cuttings was first conducted in Mariahout-Laarbeek, The Netherlands during the summer of 1999. Asexual reproduction by cuttings has shown that the unique features of this new Dahlia are stable and reproduced true to type in successive generations.

SUMMARY OF THE INVENTION

The cultivar Bronze Amazon has not been observed under all possible environmental conditions. The phenotype may vary somewhat with variations in environment such as temperature and daylength, without, however, any variance in genotype.

The following traits have been repeatedly observed and are determined to be the unique characteristics of 'Bronze Amazon'. These characteristics in combination distinguish 'Bronze Amazon' as a new and distinct pot-type Dahlia:

1. Upright, compact and rounded plant habit.
2. Freely basal branching habit, full and dense plants.
3. Semi-double type inflorescences.
4. Golden yellow and bright orange bi-colored ray florets with bright yellow-colored disc florets.

Compared to plants of the female parent, plants of the new Dahlia differ primarily in ray floret coloration as ray florets of plants of the female parent are pink in color with darker-pink towards the base. Compared to plants of the male parent plants of the new Dahlia differ primarily in ray floret coloration as ray florets of plants of the male parent are solid yellow in color.

Plants of the new Dahlia can be compared to plants of the Dahlia cultivar Margaret, disclosed in U.S. Plant Pat. No. 6,769. In side-by-side comparisons conducted in Venhuizen, The Netherlands, plants of the new Dahlia were larger, more freely branching and differed in ray floret coloration.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph at the top of the sheet comprises a side perspective view of a typical flowering plant of 'Bronze Amazon'.

The photograph at the bottom of the sheet is a close-up view of a typical inflorescence bud, developing inflorescences, upper and lower surfaces of fully opened inflorescences, and the upper and lower surfaces of typical leaves of 'Bronze Amazon'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown and flowered during the winter in Lompoc, Calif., under commercial practice in a polycarbonate-covered greenhouse with day temperatures about 18 to 24° C., night temperatures about 16 to 18° C., and light levels about 4,000 to 8,000 foot-candles. Rooted cuttings were planted in 15-cm container and plants were grown for about 18 weeks.

Botanical classification: *Dahlia variabilis* cultivar Bronze Amazon.

Parentage:

*Female, or seed, parent.*—Proprietary *Dahlia variabilis* selection identified as code number 96.2580, not patented.

*Male, or pollen, parent.*—Proprietary *Dahlia variabilis* selection identified as code number 98.3930, not patented.

Propagation:

*Type.*—Terminal tip cuttings.

*Time to rooting.*—Summer: About 8 days at 22° C. Winter: About 10 days at 22° C.

*Time to develop a rooted cutting.*—Summer: About 16 days at 20° C. Winter: About 20 days at 20° C.

*Root description.*—Fine to somewhat thick, fleshy; development of tubers has not been observed.

Plant description:

*Appearance.*—Herbaceous pot-type Dahlia. Inverted triangle; stems mostly upright and somewhat outwardly spreading giving a uniformly rounded appearance to the plant; relatively compact. Freely basal branching, about 20 lateral branches per plant; dense and full plants. Vigorous growth habit.

*Plant height.*—About 29 cm.

*Plant width or area of spread.*—About 40 cm.

*Lateral branches.*—Length: About 28 cm. Diameter: About 5 mm. Internode length: About 1.75 cm. Strength: Strong, sturdy. Texture: Smooth, glabrous. Color: 144A.

*Foliage description.*—Arrangement: Opposite; mostly simple, basal leaves, compound, trifoliate. Length, simple: About 6 cm. Length, compound: About 10.5 cm. Width, simple: About 3.8 cm. Width, compound: About 9 cm. Shape: Elliptical. Apex: Acuminate. Base: Acute. Margin: Serrate. Texture, upper and lower surfaces: Smooth, glabrous. Petiole length, simple: About 3.5 to 3.8 cm. Petiole length, compound: About 4.5 cm. Petiole diameter, simple and compound: About 4 mm. Petiole texture, upper and lower surfaces: Smooth, glabrous. Color: Young foliage, upper surface: 137A. Young foliage, lower surface: 144A. Mature foliage, upper surface: 147A. Mature foliage, lower surface: 147B. Venation, upper surface: 144A. Venation, lower surface: 147B. Petiole, upper and lower surfaces: 144A.

Inflorescence description:

*Appearance.*—Terminal and axillary semi-double type inflorescences held above and beyond the foliage on strong flexible peduncles; inflorescences face mostly outward. Composite inflorescence form with elliptical-shaped ray florets and disc florets massed at the center; ray and disc florets develop acropetally on a capitulum. Inflorescences not fragrant. Inflorescences persistent.

*Flowering response.*—Plants flower continuous and freely from April until October in Northern Europe.

*Postproduction longevity.*—Inflorescences maintain good color and substance for about one week on the plant.

*Quantity of inflorescences.*—During the flowering season, about 80 to 100 inflorescences per plant may develop.

*Inflorescence bud (stage of showing color).*—Shape: Oblate. Length: About 1 cm. Diameter: About 1.2 cm. Color: 28B.

*Inflorescence size.*—Diameter: About 4 to 5 cm. Depth (height): About 2 cm. Diameter of disc: About 1.2 cm. Receptacle height: About 5 mm. Receptacle diameter: About 1 cm.

*Ray florets.*—Shape: Elliptical, rounded. Aspect: Straight, concave. Length: About 2.2 cm. Width: About 1 to 1.2 cm. Apex: Rounded, slightly emarginate. Base: Attenuate. Margin: Entire. Texture: Smooth, glabrous, velvety. Number of ray florets per inflorescence: About 12 to 14 in about two rows. Color: When opening, upper surface: 21B. When opening, lower surface: 28B. Fully opened, upper surface: Towards apex, 13B; towards base, brighter than 33A; color does not fade with development. Fully opened, lower surface: Towards apex, 28B; towards base, 28A; longitudinal stripes, 21B.

*Disc florets.*—Shape: Tubular, elongated. Apex: Five-pointed. Length: About 6 mm. Width: Apex, about 2 mm; base, about 1 mm. Number of disc florets per inflorescence: About 80. Color: Immature: 14A. Mature: Apex: 21B. Mid-section: 14B. Base: 4A.

*Involucral bracts.*—Quantity: About 20, imbricate. Length: About 8 mm. Width: About 4 mm. Shape: Elliptical. Apex: Acute. Base: Truncate. Margin: Entire. Texture, upper and lower surfaces: Smooth, thin, membranous. Color, upper and lower surfaces: 147A.

*Peduncles.*—Length: About 7.5 cm. Diameter: About 2 mm. Strength: Strong, very flexible. Aspect: Upright. Texture: Smooth, glabrous. Color: 200D.

*Reproductive organs.*—Androecium: Present on disc florets only. Anther color: 23B. Pollen amount: Scarce. Pollen color: 14A. Gynoecium: Present on both ray and disc florets. Stigma color: 12A. Style color: 12A.

*Seed/fruit.*—Seed and fruit production has not been observed.

Disease/pest tolerance: Plants of the new Dahlia have not been observed to be tolerant to pathogens and pests common to Dahlias.

Weather tolerance: Plants of the new Dahlia have been observed to be wind and rain-tolerant; and have been observed to be tolerant to temperatures ranging from 12 to 30° C.

It is claimed:

1. A new and distinct cultivar of Dahlia plant named 'Bronze Amazon', as illustrated and described.

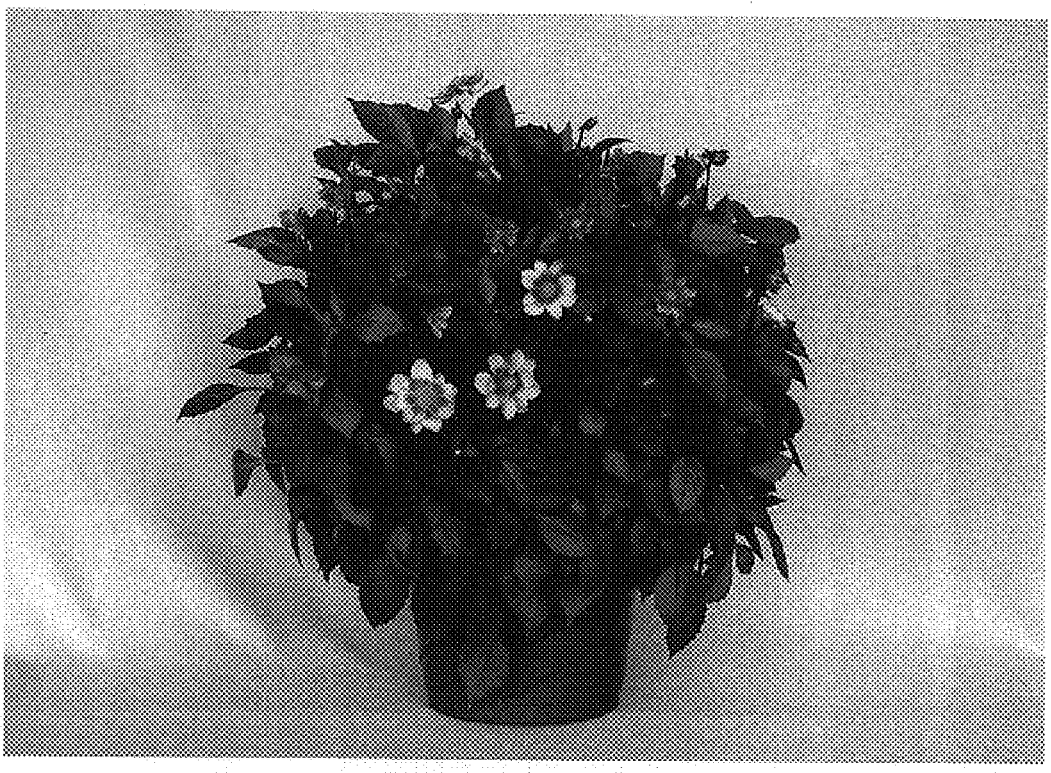
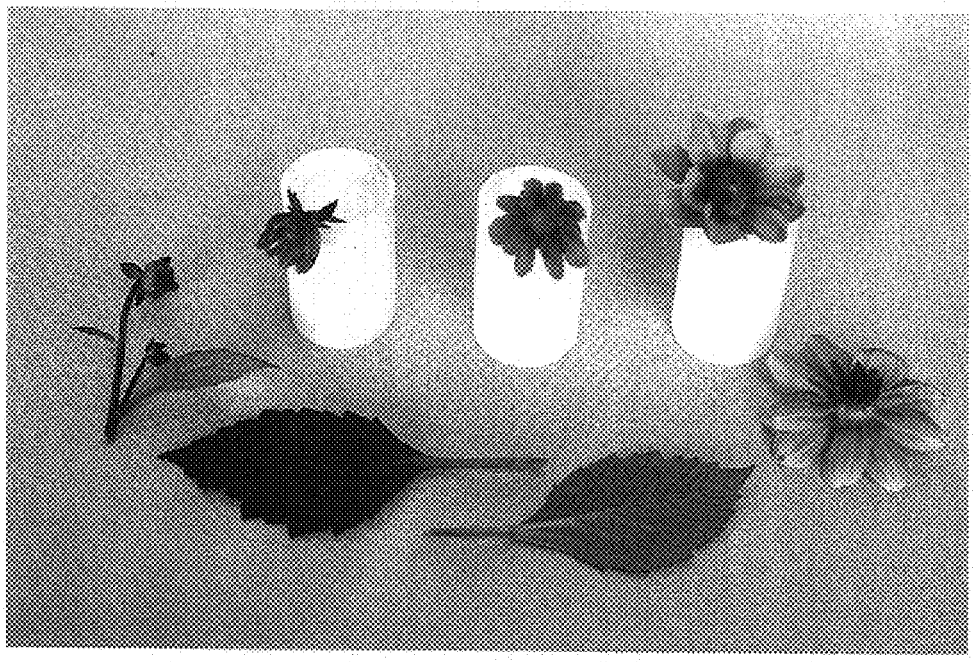

* * * * *